(12) United States Patent
Avontuur et al.

(10) Patent No.: US 6,830,714 B1
(45) Date of Patent: Dec. 14, 2004

(54) PROCESS AND APPARATUS FOR PRODUCING PARTICLES USING A SUPERCRITICAL FLUID

(75) Inventors: Petrus Paulus Cornelis Avontuur, Harlow (GB); David Roy Merrifield, Harlow (GB); Andrew Robert Souter, Harlow (GB); Christopher Edmund Valder, Harlow (GB); John Peter Warr, Harlow (GB)

(73) Assignee: SmithKline Beecham plc, Brentford (GB)

(*) Notice: Subject to any disclaimer, the term of this patent is extended or adjusted under 35 U.S.C. 154(b) by 0 days.

(21) Appl. No.: 09/868,581

(22) PCT Filed: Dec. 21, 1999

(86) PCT No.: PCT/GB99/04355

§ 371 (c)(1),
(2), (4) Date: Oct. 19, 2001

(87) PCT Pub. No.: WO00/37169

PCT Pub. Date: Jun. 29, 2000

(51) Int. Cl.[7] .................................................. B29B 9/10
(52) U.S. Cl. ................................ 264/5; 264/11; 264/12; 264/14

(58) Field of Search ................................... 264/5, 11, 12, 264/13, 14

(56) References Cited

FOREIGN PATENT DOCUMENTS

| WO | WO 95/01221 | * | 1/1995 |
| WO | WO 96/00610 |   | 1/1996 |
| WO | WO 97/31691 |   | 9/1997 |
| WO | WO 98/36825 | * | 8/1998 |

* cited by examiner

Primary Examiner—Mary Lynn Theisen
(74) Attorney, Agent, or Firm—Dara L. Dinner; Steven Venetianer; Charles M. Kinzig (57) ABSTRACT

A process, and a suitable apparatus, for production of particles of a material in which stream of a dispersion of the material in a solvent and a stream of a compressible fluid antisolvent substance are mixed under conditions such that the substance is in compressible fluid antisolvent state. The mixture then flows along a conduit (17) toward an orifice (18), from which it flows into a downstream region in which the compressible fluid antisolvent substance decompresses and the material is isolated in a particulate state. Preferably the antisolvent substance is a supercritical fluid. The process and apparatus can generate a co-formulation of the material with additives which can be introduced in a suitable aqueous or solvent based carrier vehicle.

30 Claims, 2 Drawing Sheets

PROCESS AND APPARATUS FOR PRODUCING PARTICLES USING A SUPERCRITICAL FLUID

This invention relates to a process for producing solid materials in a particulate form, and to an apparatus for performing the process. In particular this invention relates to such a process and apparatus using a substance in a supercritical fluid state.

Certain compressible fluids, e.g. gases, can act as antisolvents. An "antisolvent" is a substance which when mixed with a solvent, such as an organic solvent, reduces the power of the solvent to dissolve solutes. Consequently when an antisolvent is mixed with a solution of a solute in a solvent, the solubility of the solute can be reduced such that the solute precipitates out of solution. For example some compressed gases can act as antisolvents, for example carbon dioxide at pressures above ca. 30 bar. However the antisolvent effect of compressible fluids is most manifest when the fluid is in a supercritical fluid state.

A "supercritical fluid" as referred to herein, is a fluid at or above its critical pressure (Pc) and critical temperature (Tc) simultaneously. Such a fluid is under such conditions whereby its molar volume and solvating power can be significantly altered by varying the temperature and pressure of the fluid. Fluids which are slightly below their actual critical temperature and pressure can also show such characteristics and the term "supercritical fluid", as used herein also includes such fluids.

The use of supercritical fluids in the production of solid materials in a particulate form has been extensively documented, see for example Tom J. W. and Debenedetti P. G. "Particle formation with supercritical fluids—A review" in J. Aerosol Sci. 22(5), 555–584 (1991).

A number of processes for using supercritical fluids in the production of particles are known. These include the Rapid Expansion of Supercritical Solution ("RESS") process, see for example Tom J. W. and Debenedetti P. G. (op cit), the Gas Anti-Solvent ("GAS") process, see for example Gallagher P. M. et al, "Supercritical fluid science and technology", ACS Symp. Ser., 406, p334 (1989), and the Solution Enhanced Dispersion using Supercritical Fluids ("SEDS") process, see for example University of Bradford GB 2322326A, PCT/GB94/01426 and PCT/GB95/01523.

Current GAS processes using supercritical fluids in the production of particles isolate particles of a solute by precipitation from a solution using a supercritical fluid such as carbon dioxide as an antisolvent. They are generally batch processes where the solute product is difficult to remove from the particle formation chamber and where other shortcomings exist. Fine particles resulting from rapid crystallisation processes can undergo crystal growth during the prolonged exposure to the supercritical fluid in these processes and changes to the material can occur during the depressurisation cycle required to harvest the product. Small, well engineered and controlled particles, desirably approaching or below one micron, are difficult to achieve using known supercritical fluid GAS processes of the type referred to above. WO 97/31691 (University of Kansas) discloses a process for particle precipitation and coating using a GAS supercritical fluid process.

Processes such as RESS rely on saturator chambers to dissolve material prior to particle formation. These are semi continuous processes that can last for some hours and again shortcomings exist. As the saturator is depleted the resulting solution can vary in concentration. In addition, the material within the saturator may be subjected to degradation or a change of physical form at the elevated times, temperatures and pressures involved.

In the SEDS process and apparatus a mixture of a supercritical fluid and a solvent is allowed to expand into a downstream particle formation vessel, which is provided with a back pressure regulator. The SEDS process involves a complex nozzle structure and a back pressure regulator.

It is an object of the present invention to provide an alternative, improved process using supercritical fluids in the production of particles, which in part at least solves the problems of these prior art processes. Other objects and advantages of the present invention will be apparent from the following description.

DESCRIPTION OF THE INVENTION

According to this invention, a process for using a compressible fluid antisolvent substance in the production of particles of a material is provided wherein:

a stream of a dispersion of the material in a solvent and a stream of a compressible fluid antisolvent substance are brought into contact with each other so that the streams combine to form a mixture under conditions such that the substance is in a compressible fluid antisolvent state, the mixture is then caused to flow along a conduit extending downstream from the region where the streams come into contact, toward an orifice opening from the conduit, the pressure and temperature of the mixture in the conduit being such that the compressible fluid antisolvent substance remains in a compressed state over at least part of the length of the conduit, then the mixture is caused to flow into a downstream region in which the compressible fluid antisolvent substance decompresses into a gaseous state and the material is isolated in a particulate state.

In a second aspect this invention further provides an apparatus suitable for performing the process of this invention.

Such an apparatus may comprise:

means for bringing a stream of a dispersion of the material in a solvent and a stream of a compressible fluid antisolvent substance into contact with each other such that the streams combine to form a mixture under conditions such that the substance is in a compressible fluid antisolvent state, a conduit extending downstream from the region where the streams come into contact toward an orifice, along which the mixture can flow, means to cause the pressure and temperature of the mixture in the conduit to be such that the substance remains in a compressed state along at least part of the conduit, a region in downstream communication with the orifice in which region the pressure and temperature conditions are such that the compressible fluid antisolvent substance decompresses and the material is recovered as a solid.

Preferably in its compressed state the substance is in a compressible fluid antisolvent state.

In a preferred embodiment of this invention the compressible fluid antisolvent substance is in a supercritical fluid state, and when the substance decompresses the substance expands and converts into a gaseous state, and the material is recovered as a solid.

Therefore in this preferred embodiment of the process of the invention, a process for using a supercritical fluid in the production of particles of a material is provided wherein:

a stream of a dispersion of the material in a solvent and a stream of a supercritical fluid substance are brought into contact with each other so that the streams combine to form a mixture under conditions such that the substance is in a supercritical fluid state, the mixture is then caused to flow along a conduit extending downstream from the region where the streams come into contact, toward an orifice opening from the conduit, the pressure and temperature of the mixture in the conduit being such that the substance remains in a supercritical fluid state over at least part of the length of the conduit, then the mixture is caused to flow into a downstream region in which the pressure and temperature conditions are such that the substance converts into a gaseous state and the material is isolated in a particulate state.

An apparatus is also provided for performing this preferred process, comprising:

means for bringing a stream of a dispersion of the material in a solvent and a stream of a supercritical fluid substance into contact with each other such that the streams combine to form a mixture under conditions such that the substance is in a supercritical fluid state, a conduit extending downstream from the region where the streams come into contact toward an orifice, along which the mixture can flow, means to cause the pressure and temperature of the mixture in the conduit to be such that the substance remains in a supercritical fluid state along at least part of the conduit, a region in downstream communication with the orifice in which region the pressure and temperature conditions are such that the substance converts into a gaseous state and the material is recovered as a solid.

The term "orifice" as used herein includes an outlet, opening or hole which allows a restricted flow, e.g. a part of the conduit which is narrower than an upstream part of the conduit, or a valve.

The term "compressible fluid antisolvent substance" as used herein includes a fluid whose density can be varied by changes in pressure resulting in a change in the ability of the substance to dissolve material of interest. Typically such a fluid displays a lower ability to dissolve the material than the solvent.

Preferably in the process and apparatus of this preferred aspect of the invention the mixture is caused to flow through the orifice into a downstream region in which the pressure and temperature conditions are such that the supercritical fluid substance converts into a gaseous state and the material is isolated in a particulate state.

The term "dispersion" as used herein includes true solutions in which the material is in solution as a solute in the solvent, and also suspensions in which solid particles or liquid droplets of the material (e.g. if the temperature of the dispersion is above the melting point of the material) are suspended in the solvent, and which may contain some dissolved material. Derived terms such as "dispersed" are understood correspondingly.

Particle formation may occur in the process and the apparatus at any point after mixing of the streams. For example in the mixture the material may be dissolved in the solvent and/or mixture and particle formation may occur via a RESS type process. Additionally or alternatively the material may be dissolved in the solvent and particle formation may occur via a GAS type process in which the material comes out of solution due to the antisolvent effect of the compressible fluid antisolvent substance, particularly when this is the preferred supercritical fluid substance.

The process of this invention may be fully continuous and in part at least overcomes at the problems of prior art processes for using supercritical fluids in the production of particles highlighted above. There is no need for a saturator chamber and the residence time of the material in supercritical fluid may be minimised.

The process of the invention is particularly suitable for use with materials which are pharmaceutical materials, e.g. drug materials. For example the process is suitable for processing such materials where particles of defined form are required for making into oral dosage forms e.g. tablets, pills etc. or for particulate inhalation.

Suitable substances which can be used as the compressible fluid antisolvent substance include nitrogen, ethane, ethylene, carbon dioxide, nitrous oxide, sulphur hexafluoride, xenon and halocarbons such as trifluoromethane and chlorofluoromethanes e.g. chlorotrifluoromethane. However carbon dioxide is preferred, inter alia because it is cheap, non-flammable, non-toxic and environmentally benign (though allegedly a "greenhouse" gas), and is preferred in the present process. For example carbon dioxide at a pressure above ca. 30 bar, e.g. 40 bar or higher may be used. The substance may be recycled so that environmental pollution may be minimised.

Suitable substances which can be used as the supercritical fluid substance are those generally known to those skilled in the art, e.g. ethane, ethylene, carbon dioxide, nitrous oxide, sulphur hexafluoride, xenon and halocarbons such as trifluoromethane and chlorofluoromethanes e.g. chlorotrifluoromethane, as listed above. Supercritical fluid water may also be used in some applications. However carbon dioxide is again preferred. The supercritical fluid substance may optionally include one or more modifiers, which may change the intrinsic properties of the supercritical fluid in or around the critical point. Suitable modifiers are known in the art and include for example methanol, ethanol, isopropanol and acetone, which if present may constitute up to 20% of the supercritical fluid substance.

Suitable conditions of temperature and pressure to achieve a supercritical state for such materials are known from the literature, for example in the case of carbon dioxide from Perry's Chemical Engineers Handbook. Typically the pressure and temperature of the supercritical fluid substance is likely to be in the range 1.01 Tc –4.0 Tc and 1.01 Pc–7.0 Pc. For example carbon dioxide has a Tc of 31° C. and a Pc of 74 bar, and suitable conditions of temperature and pressure to generate a supercritical fluid state are 35–250° C. and a pressure of 40–300 bar, preferably 40–80° C. and 50–120 bar, typically ca. 70° C. and ca. 80 bar.

It may be desirable to use an operating temperature in the conduit and inlets which is below the melting point of the material, and which may for example be below the Tc of the compressible fluid antisolvent substance. Also it may be desirable to use lower temperatures to increase the density of a supercritical fluid substance. Use of a high pressure to ensure that the substance is in the supercritical fluid state may also be desirable.

Suitable solvents, especially for dissolution of the material, include organic solvents such as $C_5$ alkyl $Cl_5$ alkanoate esters such as ethyl acetate, $C_{1-5}$ alcohols such as methanol, and di- $C_5$ alkyl ketones such as acetone, water, and mixtures thereof, such as an alcoholketone mixture such as a methanol-acetone mixture. Other solvents e.g. as used in known GAS processes, such as halogenated organic solvents may also be used. The solvent may be introduced as a two-phase system (liquid and vapour).

Suitable solution concentrations for the dispersion, e.g. a solution, of material may be determined experimentally e.g. 1–1000 g per L, e.g. 80–200 g per L, typically ca. 100 g per L. Typically the solvent may be saturated or near saturated with the material, but the process of the invention may also be used with non-saturated and dilute solutions. Suitable concentrations of the material in the dispersion and the mixture, e.g. solution concentrations, can be determined experimentally. The presence of solvent(s) in a supercritical fluid will change the solvent capacity of the supercritical substance. Mixtures of solvents have the advantage that if the solubility of the material is lower in one component of such a mixture than in another component, the degree of saturation of a solution of the material in such a mixture of solvents may be changed without changing the overall concentration, which from processing or other considerations it may be desirable to fix. A methanol-acetone mixture is preferred because both acetone and miethanol are miscible with supercritical carbon dioxide.

For example in a preferred embodiment of the process and apparatus of this invention a "T" or "Y" tube system may be used to bring the dispersion of the material and the compressible fluid antisolvent substance, e.g. the supercritical fluid substance, into contact with each other and to provide the conduit. For example the material may be dispersed, e.g. dissolved as a solute in a suitable solvent, preferably an organic solvent as described above, and the solution may be metered to one limb (the term "limb" used herein refers to any of the vertical stem or the side arms of a "T" or "Y" figure) of a T or Y tube, in a temperature controlled oven. To another limb of the temperature controlled T or Y tube is metered the compressible fluid antisolvent substance, preferably in a supercritical fluid state, such as compressible, preferably supercritical, carbon dioxide. In such an arrangement the third limb of the T or Y comprises the conduit. The junction of the limbs may be a simple "T" or "Y" junction or a mixing chamber, e.g. an enlargement of the tubes, may be provided at the junction.

In at least the third limb, and at the junction of the limbs, the temperature and pressure are maintained such that the substance is in a compressible fluid antisolvent state, in the preferred form of the process, in a supercritical state. Preferably the substance remains in a supercritical fluid state over the entire length of the conduit, e.g. from the junction of the limbs to the orifice. For example in the case of preferred carbon dioxide the abovementioned typically ca. 70° C. and ca. 80 bar are representative of suitable temperature and pressure conditions to achieve a supercritical fluid state.

Suitable flow rate ratios of the compressible fluid antisolvent substance, e.g. supercritical fluid, substance: dispersion may be determined experimentally. A supercritical fluid substance: dispersion, e.g., solution, ratio of 50 or less: 1 is preferred for example in the range 50:1–10:1, for example typically around 30:1–15:1. At the junction of the limbs of the T or Y tube the two streams meet and mixing commences. Mixing may also occur and/or continue as the solution and the compressible fluid antisolvent substance flow along the third limb of the T or Y.

In this embodiment of the process and apparatus the orifice may be provided at the downstream end of the conduit, for example when the conduit comprises a limb of the above-mentioned T or Y tube the orifice may be at the end of the limb remote from the junction of the limbs.

Introduction of Additives and Modifiers

In a further embodiment of the process of this invention one or more additives and/or modifiers may be introduced into the mixture of the material, the solvent and the compressible fluid antisolvent substance, and for this purpose the apparatus may provided with introduction means for the introduction of such additive(s) and/or modifiers. Such one or more additives may be liquids or solids or mixtures thereof. For example the additive, especially a solid additive, may be introduced as a dispersion (as defined above) in a suitable carrier vehicle, typically a liquid or gas. If one or more of such additive(s) is a solid or liquid the effect of introducing the additive can be co-formulation of the material and the additive, and the product of this embodiment of the process may be a mixture of the solute and the additive. The quantity and proportions of the additive relative to the material can be advantageously precisely metered.

Such one or more additives may be introduced at various points in the process and apparatus of this invention.

For example the additive, e.g. a solid additive, may be introduced as a dispersion (as defined above) in a suitable carrier vehicle into the input stream of dispersion of the material and/or the compressible fluid antisolvent substance, and the apparatus may be provided with suitable introduction means for this purpose. Additionally or alternatively the additive, including its carrier vehicle if used, may be mixed with one or both of the input streams for example by dissolving or suspending the additive in the dispersion of material before this is inputted.

Additionally or alternatively the one or more additive may be separately introduced into the region where the streams mix, and the apparatus may be provided with suitable input means for this purpose.

Additionally or alternatively such an additive, e.g. a solid additive together with its carrier vehicle if used, may be introduced into the mixture of the dispersion and the compressible fluid antisolvent substance at the region where the streams of dispersion and compressible fluid antisolvent substance contact each other, via suitable introduction means in the apparatus. For example the introduction means for the additive at the region where the streams of solution and compressible fluid antisolvent substance contact each other may comprise an "X" tube arrangement, the respective streams of dispersion of material and compressible fluid antisolvent substance being for example introduced via two respective limbs of the "X" tube arrangement, the additive, including its carrier vehicle if used, may be introduced into the flow via a third limb of the "X" tube, and the fourth limb of the "X" may comprise the conduit. In this arrangement the orifice may be at the end of the fourth limb remote from the junction of the limbs.

Additionally or alternatively such additive(s), including its carrier vehicle if used, may be introduced into the mixture of the dispersion and the compressible fluid antisolvent substance in the conduit between the region where the solution and the compressible fluid antisolvent substance meet and the orifice, via suitable introduction means in the apparatus located to feed the additive into the conduit. For example the introduction means for the additive and its carrier vehicle, if used, into the conduit may comprise a further "T" or M "Y" tube arrangement, located downstream of the point where the dispersion and compressible fluid antisolvent substance meet. For example the conduit may comprise two limbs of such a "T" or "Y" tube along which the mixture of dispersion and compressible fluid antisolvent substance flow, and the additive and any fluid vehicle if used may be introduced into the flow via the third limb of the "T" or "Y, tube.

The additive, including its carrier vehicle if used, may be introduced into the mixture at a point downstream of the part of the process and apparatus where the compressible fluid antisolvent substance decompresses, e.g. where a supercritical fluid substance converts into a gaseous state, and the material separates as a solid.

Such an additive may be an excipient material as understood in pharmaceutical technology. An excipient material may for example comprise a carrier material, filler or matrix-forming material such as inert inorganic materials such as silica, cellulose and cellulose derivatives such as hydroxypropylmethyl cellulose, polysaccharides such as sugars, e.g. mannitol, surface active agents (some surface active agents are liquids) and other surface modifying agents such as sodium lauryl sulphate. An excipient material may also comprise a coating material which coats particles of the material. For example if the dispersion contains solid particles of the material these may be coated with a dissolved excipient as this comes out of solution, e.g. via expansion of the mixture in the downstream region.

The carrier vehicle may for example be a solvent or suspension substance, such as an organic liquid. The carrier vehicle may be an aqueous fluid for example water itself or water in admixture with an organic liquid. Such an aqueous fluid may have the advantageous effect of encouraging the formation of particles of the solvent material from the mixture by means of an antisolvent effect, and may for example be a good solvent for a dissolved excipient.

If a fluid carrier vehicle is used, the composition of the mixture of carrier and additive may be determined experimentally to suit any particular requirement, for example to provide a desired proportion of excipient materials in admixture with the solute. The proportion of material to excipient may vary over wide ranges depending upon the nature of the material and excipient, for example only a small proportion of a surfactant may be needed, but a matrix-forming excipient may comprise the bulk of a co-formulation with a material. In the case of placebo formulations the product may be 100% excipients such as a filler or matrix forming excipient. For example the excipient may be introduced in a ratio excipient: material of 0.01–100:1. The concentration of additive, e.g. excipient in any carrier vehicle may be determined experimentally to suit particular purposes.

Modifiers, which are liquids or gases may be used to adjust the solvent capacity of the solvent, the compressible fluid antisolvent substance, or the mixture thereof, and may be additionally or alternatively introduced at the above-mentioned points in the process and apparatus where additives may be introduced. As mentioned above, suitable modifers include methanol, ethanol, isopropanol and acetone.

The above described process, and apparatus for performing the process, in which a mixture of a material and the additive is produced by introducing the additive, typically as a suspension or solution in a fluid carrier vehicle, into a stream comprising the material and a compressible fluid antisolvent substance particularly a supercritical fluid substance, typically in the presence of a solvent for the material, under conditions at which the substance is in a compressible fluid antisolvent, e.g. supercritical fluid, state, and then causing the mixed stream to flow into a downstream region where the compressible fluid antisolvent substance decompresses, is believed to be novel and is a further aspect of the invention.

Pressure and Temperature Control

The pressure and temperature of the mixture of components in the process of this invention may be controlled by various techniques in the process and apparatus of this invention.

In one technique the pressure and temperature of the mixture, whether or not a additive is introduced, in the conduit are maintained by means of the dimensions of the conduit being such as to generate a back pressure in part or all of the conduit between the region where the streams meet and the orifice. The length of such a conduit should be such that the residence time of the mixture in the conduit is such that particle formation occurs in the conduit. For example the conduit may be a tube of substantially greater length than its bore.

For example conduit lengths of 0.1 cm to 5000 cm, preferably 1–100 cm with internal bores 0.01 to 1 mm may be suitable to maintain such a back pressure using the flow conditions mentioned herein relation to the process of the invention, but other suitable dimensions e.g. in a scale up of the process to production scale, may be determined experimentally. Such dimensions may of course be scaled up, or several such conduits may be used in parallel to provide an industrial scale process.

In another technique a pressurised gas may be introduced into the flow of mixture between the region where the streams meet and the orifice, i.e. in the conduit, and the apparatus may be provided with suitable pressurised gas introduction means to do this. In this technique the conduit may again be a tube of substantially greater length than its bore. The introduction of the pressurised gas can help the pressure and temperature of the mixture in the conduit to be such that the compressible fluid antisolvent substance remains in a supercritical fluid state, thereby avoiding the need for a back pressure regulator, which can tend to become blocked, enabling use of a mechanically simplified apparatus. Additionally the pressurised gas can help to keep the conduit and/or orifice clear of blockages and can help to strip away the solvent from the formed particles.

As mentioned above the pressure of the introduced pressurised gas can generate a back pressure and temperature in that part of the conduit to maintain the compressible fluid antisolvent substance in a supercritical state, in particular between the point where the streams combine and the point where the pressurised gas is introduced.

The pressurised gas introduction means may comprise means to introduce the pressurised gas directly into the conduit. For example this may comprise a side inlet into the conduit by which the pressurised gas may be introduced into the conduit.

For example the conduit may itself be in the form of a "T" or "Y" tube, with the conduit comprising two limbs of the T or Y tube, and the side inlet comprising the third limb of the T or Y. The inlet may be positioned anywhere between the point where the streams of dispersion and compressible fluid antisolvent substance such as a supercritical fluid meet and the orifice, e.g. anywhere along the length of the conduit, but it may be preferable to position the side inlet close to the orifice, e.g. within 30% of the distance from the orifice to the point where the streams meet, or where the additive is introduced. By introducing the pressurised gas at this position upstream of the orifice it is possible to ensure that the pressurised gas generates a back pressure upstream of the orifice, thereby enabling the mixture in the conduit upstream of the point where the pressurised gas is introduced to be at a suitable pressure, for example so that the substance is in a supercritical fluid state. It is preferred to introduce the pressurised gas downstream of the point in the conduit where particle formation occurs, so as for example to ensure that particle formation occurs in a supercritical fluid environment. This point can be determined experimentally.

Any pressurised gas may be used which in practical terms is inert relative to the material, the solvent, the compressible fluid antisolvent substance and additives if used. For example suitable gases include nitrogen, air or carbon dioxide. Typically the introduced gas may be at a pressure of for example 50–100 bar, for example ca. 100 bar. The pressurised gas may be pre-heated to a suitable temperature, e.g. substantially the same temperature as the mixture in the conduit, prior to introduction into the mixed streams to reduce the likelihood of cooling of the mixed stream.

In another control technique, where the fluid mixture of components formed at any stage of the above-described process flows along the conduit in a high pressure upstream to a lower pressure downstream direction, the flow of the mixture is restricted in the conduit, between an upstream high pressure zone and a downstream lower pressure zone, and a flow control fluid is introduced into the conduit upstream of the restriction, the pressure of the flow control fluid being equal to or greater than the pressure of the flowing fluid upstream of the restriction.

Suitably the apparatus may include a restriction in the conduit, and may be provided for introducing such a flow control fluid into the conduit at the upstream side of the restriction.

This technique in the process and apparatus can enable control of the pressure in the flowing fluid either downstream or upstream of the restriction between two zones at different pressures. This way of control can be less sensitive to fouling and can provide a means of preventing condensation or solidification of an expanding flowing fluid.

The restriction may be any narrowing of the conduit, for example the restriction may be an orifice or a valve or a piece of conduit which is narrower than an upstream piece of the conduit. In order that the flow rate be controllable, the cross sectional area of the conduit at the restriction should be equal or larger than required at the maximum flow of the flowing fluid between the parts of the conduit upstream and downstream of the restriction for the given pressure differential between these parts.

The restriction may be placed at any position in the conduit, for example at a point along the conduit along which the fluid mixture flows, or at a point where the conduit meets an expansion vessel. For example the orifice may be located upstream, suitably immediately upstream, of the orifice in the process and apparatus of the invention, e.g. at the point where the orifice meets the downstream region. By this means the pressure upstream of the orifice and the flow through the orifice may be controlled.

The relation between the flow rate to be controlled, the flow rate of the control fluid and the cross sectional area of the restriction can be determined using engineering calculations.

The flow control fluid may also be a gas or liquid. The flow control fluid may for example be the same substance as the compressible fluid antisolvent substance. The flow control fluid may for example comprise the above-mentioned pressurised gas, and introduction of this pressurised gas may be used to control the system.

The flow control fluid is introduced into the stream of the flowing fluid upstream of the restriction, and may for example be introduced into the conduit by means of one or more side inlets. The flow control fluid may be introduced immediately, or a short distance, upstream of the restriction. The pressure of the flow control fluid prior to nixing with the mixture of components in the conduit should be at least equal to the maximum pressure of the flowing fluid immediately upstream of the restriction to ensure that the flow control fluid flows into the flowing fluid and for example that the flowing fluid does not undesirably enter a side inlet. By varying the flow rate of the flow control fluid, the pressure upstream of the restriction can be controlled independent of the flow rate of the flowing fluid. For example when the flow rate of the flow control fluid is zero, the flow rate of the flow fluid can be at a maximum.

When the flow rate of the flow control fluid is at its highest the flow rate of the flowing fluid is near zero and dependent upon the pressure of the flow control fluid prior to mixing. In such a situation the restriction may resist flow of the flow control fluid and thereby generate a back pressure upstream of the restriction to restrain flow of the flowing fluid. If the pressure of the flow control fluid is above the pressure of the flowing fluid upstream of the restriction the flow control fluid will act as a pressure lock between a high pressure zone upstream of the restriction and a low pressure zone downstream of the restriction. If the pressure of the flow control fluid is equal to the pressure in the zone upstream of the restriction, no flow of the flowing fluid takes place. Advantageously however such an arrangement is able to vent pressure surges from the high-pressure zone. If the pressure of the flow control fluid is slightly below the pressure in the zone upstream of the restriction of the flow control fluid, a bleed flow of the flowing fluid occurs from the high pressure zone to the low pressure zone.

Some diffusional flow may take place from the high-pressure zone to the lowpressure zone. The device and method of this invention may be arranged to minimise diffusional flow.

The pressure and flow rates of the respective flowing fluid and the flow control fluid may be controlled using equipment, e.g. pressure and flow sensors, valves etc. conventional to the art of fluid control. For controlling the pressure of a flowing fluid in a high-pressure zone upstream of the restriction, independently of the flow rate of the fluid the following control mechanism may for example be used.

A pressure sensor may be placed in the high-pressure zone, upstream of the point where the flow control fluid is introduced into the flowing fluid. The signal from this sensor is used to control the flow rate of the flow control fluid e.g. using control systems which are apparent to those skilled in the art. Various types of control systems can be used to control the flow rate of the flow control fluid, such as an actuated valve or a controllable pump. Alternative control systems will be apparent to those skilled in the art.

Disadvantageous condensation or solidification of the flowing fluid stream can occur because of the cooling effect of expansion. Thus, in order to prevent condensation or solidification, heat may need to be transferred to an expanding fluid. Direct mixing of the expanding fluid with a heat carrier is the most rapid way in which to achieve this. For example in the process of the present invention a heat carrier fluid may be introduced into the mixture flowing along the conduit. In the present invention the flow control fluid may itself be a heat carrier, and its temperature may be selected or controlled to prevent condensation or solidification. As an example, if carbon dioxide at 70° C. and 150 bar expands adiabatically, then liquid carbon dioxide or dry ice is formed at pressures below 73 bar. By addition of excess nitrogen, air or carbon dioxide of a temperature well in excess of 70° C., expansion to atmospheric pressure is possible without the formation of dry ice.

For example the flow control fluid may be pre-heated prior to introduction into the flow of the flowing fluid. A suitable temperature to which the flow control fluid may be pre-heated may be determined by monitoring the flowing fluid downstream of the restriction, e.g. for the presence of condensation or solidification.

The above control techniques may be used together or separately.

Such parameters of the process and apparatus of this invention as the input flow conditions of the dispersion, the compressible fluid antisolvent substance, the additive and fluid, and the flow control fluid, for example into respective limbs of "T", "Y" or "X" tube arrangements, the length and/or bore of the conduit, the dimensions of the orifice, the position in the conduit at which the additive (if used), or the pressurised gas (if used) is introduced and the pressure at which the gas is introduced, are selected to give a back pressure in the conduit between the point where the streams of the dispersion and the supercritical fluid substance mix and the orifice, which ensures that at the temperature within the conduit the substance is at, or near, supercriticality. For example in the case of preferred carbon dioxide at the abovementioned typically ca. 70° C. a back pressure of ca. 80 bar is suitable. The input conditions, e.g. input pressure and input rate of the further fluid and/or pressurised gas are relatively easily controlled and provide a convenient means by which the back pressure in the conduit may be easily tuned, for example to maintain the substance in the conduit in the preferred supercritical state.

Orifice and Downstream Region.

The orifice may comprise the open end of a narrow-bore, e.g. capillary, tube e.g. the open end of a narrow-bore conduit. Alternatively the orifice may be separately provided at the end of the conduit e.g. as one or more laser-drilled holes. The orifice may comprise part of a spray head including multiple orifices, or a particulate solids-tolerant valve.

Downstream of the orifice is a downstream region in which the pressure and temperature conditions are such that the compressible fluid antisolvent substance decompresses, and if it is a supercritical fluid expands into a gaseous state and the solvent is removed from the material to yield particles. Suitable conditions of temperature and pressure for any particular application may be determined experimentally, but for the supercritical fluid substances and solvents referred to herein typically in the downstream region the pressure may be 1–20 bar, preferably for example around atmospheric, and the temperature may be 0–50° C., for example around ambient temperature. The orifice may open directly into the downstream region. It may be desirable to warm the environment of the downstream region such that residual solvent is carried from the product by an excess of the substance in a gaseous state. In the apparatus of the invention the downstream region may comprise an expansion chamber.

In the process of the invention it is also desirable to arrange for collection of the particles which are formed, and the apparatus of the invention may be provided with a downstream region for collection of the particles. The apparatus may for example incorporate a means for collection of the particles, e.g. a cyclone for separation of the particles from the expanded gas stream and/or a filter for the retention of the particles. The mixture exiting from the orifice contains fine particles which are collected in the downstream region. For example an outlet from the expansion/collection chamber, along which the gaseous outlet from the collection chamber may flow, may lead to such a filter and/or cyclone by which the particulate product is collected.

For some applications, particularly when the riixture emerging at the orifice contains water, e.g. if as mentioned above an aqueous carrier vehicle has been used to introduce an additive, it may be desirable to provide drying means in the downstream region to remove solvent and especially water from the product. Suitably the drying means may entrain the particles in the downstream region in a stream of, preferably heated, gas which may for example be an inert gas or air. Accordingly in the process of the invention materials carried in an aqueous vehicle may be dried and water may be removed, and the apparatus of the invention may incorporate a drying means for this purpose. In the apparatus of the invention a spray drier of generally known type may be used for this purpose, and the conduit may be used as the input feed line of such a spray drier. For example the spray head of the spray drier may comprise the orifice, or the orifice may be used as the spray head of an otherwise conventional spray drier. In such a construction means are provided to introduce a stream of heated gas, e.g. air around the orifice, where it flows around the orifice, entrains and dries the particles formed in the process. The flow of gas, e.g. air may pull the stream of particles into the downstream expansion chamber.

For example the orifice may comprise a spray head at the upper part of an expansion chamber, and the spray head and/or upper part of the chamber may be heated by a suitable heater. Air may be drawn through the heater and around the spray head, where it entrains the particles formed in the process. The air-particle suspension may be pulled in through the expansion chamber, where it dries, and into a cyclone separator. For example the outlet flow from the downstream expansion chamber may lead to a spray dryer/coliector, such as a Buchil" spray dryer, containing both a cyclone and a filter such into as a "HEPA" (High Efficiency Particulate Air) filter. The solid particles may be separated out and collected in the cyclone, whilst the air and gases resulting from the expansion is exhausted via the HEPA filter.

The parts of the apparatus of the invention which come into contact with the dispersion, the compressible fluid solvent, additive, vehicle, compressed gas etc., e.g. the "T", "Y" or "X" tube arrangement of the apparatus may be constructed of inert metal such as stainless steel or other inert material. For example the T, Y or X tube may comprise narrow bore steel tubing. It is desirable to use such tubing of as wide a bore as practical, to reduce blocking. Tubing of bore 0.1–1.00 mm has been found suitable, but clearly for an industrial scale process wider bore tubing may be used, and/or more than one of the above-described apparatus may be used in parallel.

The apparatus may also include means for recovering the solvent and/or the compressible fluid solvent substance, e.g. the carbon dioxide, and optionally recycling this. The apparatus may comprise more than one such downstream region, thereby allowing for the substantially continuous operation of the apparatus through switching from one downstream region to another, e.g. via a valve arrangement on the conduit. The downstream region may be a closed chamber, making it easy to maintain sterile conditions and reducing the risk of environmental pollution or contamination of the product particles with the atmosphere or moisture.

Suitably the material processed in the process and apparatus of the invention may be a pharmaceutical material, and the process and apparatus of this invention may be used to isolate such materials as fine particles of a desirably small size e.g. around 1–20 micron.

Consequently in a third aspect the invention provides a particulate product material made using the process and/or the apparatus of this invention.

The invention will now be described by way of non-limiting example only with reference to FIGS. 1, 2 and 3 of the accompanying drawings which schematically show apparatus of this invention, and FIG. 4 which shows a control technique using a flow control fluid.

EXAMPLE 1

Figure 1:
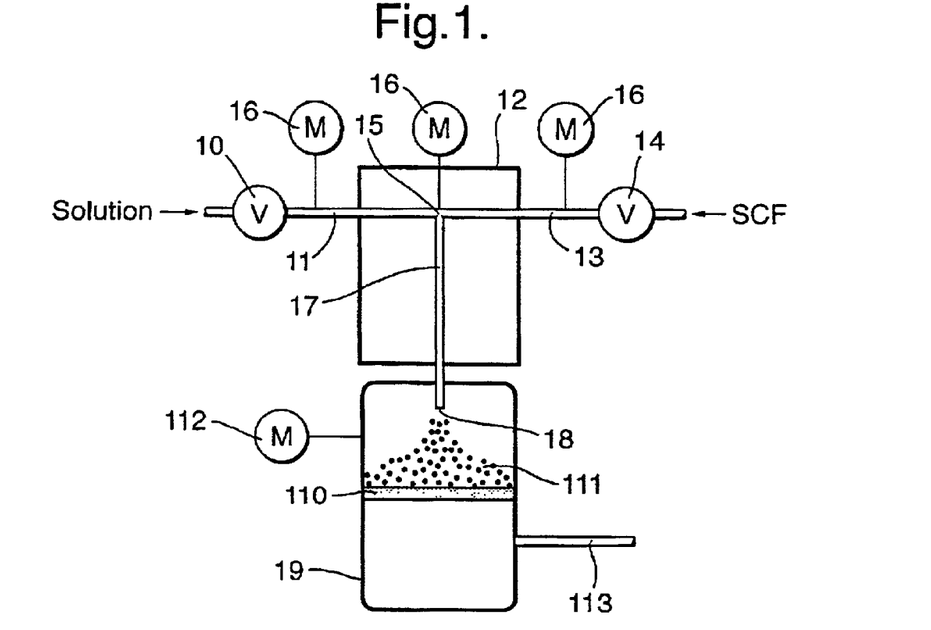

Referring to FIG. 1 one apparatus for performing the process of the invention is disclosed.

A material being an organic carbapenem antibiotic compound together with 1% ww of a surface active agent docusate sodium is dissolved in ethyl acetate at a solution concentration of 10 mg/ml, and this solution is metered at a flow rate of 1 ml/min, via a pump (not shown) through metering valve 10 to one limb 11 of a T tube in a temperature controlled oven 12.

Carbon dioxide is metered to another limb 13 of the temperature controlled T tube, via metering valve 14. This carbon dioxide is obtained from a high pressure source of the gas (not shown). Means are well known in the art for providing carbon dioxide from such a source in a suitable manner for it to be used in a supercritical fluid process. In the limbs 11 and 13, and at the junction 15 of the limbs 11 and 13, the temperature and pressure are monitored by monitors 16 and maintained by means of the temperature control of the oven 12, valves 10 and 14, and the pumps etc. (not shown) used to deliver the respective dispersion and carbon dioxide, such that the carbon dioxide is maintained in a supercritical state, a temperature of 70° C. and 80 bar being used. Limbs 11, 13 of the T tube were made of stainless steel tubing of internal bore 0.75 mm, 0.1 to 1 mm internal bore also being investigated and found to be suitable.

At the junction 15 of the limbs 11 and 13 of the T tube the respective streams of solution and supercritical carbon dioxide meet and mix. The mixture of solution and supercritical carbon dioxide then flows down a narrow-bored conduit 17 extending downstream from the junction 15 of the limbs 11 and 13, being the stem of the T tube. The length of the conduit 17 is such that between the junction 15 and a downstream orifice 18 being the open end of the conduit 17, a back pressure is generated such that in the conduit the carbon dioxide remains in a supercritical state, for example at the above-mentioned typically ca. 70° C., a back pressure of ca. 80 bar is a suitable back pressure.

In the experiment described the conduit 17 had a length of 55 cm between the junction 15 and the orifice 18, with an internal bore of 0.1 mm.

The orifice 18 opens into a pressure and temperature controlled environment, i.e. an expansion chamber 19, in which the temperature and pressure conditions are such that the carbon dioxide expands into a normal gaseous state, for example a temperature of ca. 20° C. and atmospheric pressure being suitable. In the chamber 19 a co-formulation of the solute carbapenem and the surfactant separates from the flow and collects in a filter 110 in the vessel 19 as fine particles 111, of needle form ca. 8 microns long and useful for pharmaceutical purposes. The pressure and temperature in the vessel 19 are monitored by monitor 112. Excess carbon dioxide and solvent vapour exit from vessel 19 via exit chimney 113, which may lead to a fines filter (not shown). Temperature in vessel 19 is controlled by a heater means of known type (not shown).

EXAMPLE 2

Figure 2:
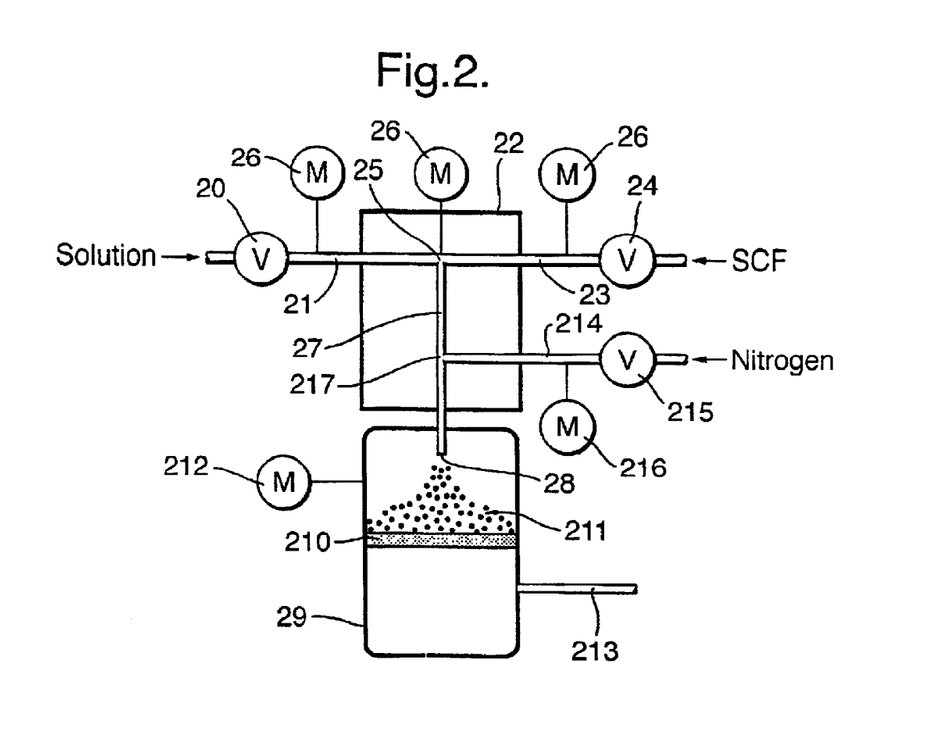

Referring to FIG. 2 another apparatus for performing the process of the invention is disclosed. In FIG. 2 parts corresponding to those of FIG. 1 are numbered correspondingly, (i.e. the features in FIG. 2 corresponding to features 10, 11, 12 etc. in FIG. 1 are numbered 20, 21, 22 etc. in FIG. 2) and the tube dimensions, temperatures, pressures etc. used in the apparatus of FIG. 2 were as described above with reference to FIG. 1. In the apparatus of FIG. 2 the conduit 27 had a length of 10 cm between the junction 25 and the orifice 28, with an internal bore of 0.75 mm, i.e. the same bore as the T tube limbs 21, 23.

The conduit 27 of FIG. 2 is itself in the form of a T tube, having a side inlet tube 214 of the same 0.75 mm bore tubing as the conduit 27 itself. 0.15 mm bore tubing was also investigated and found suitable. In the experiment the side inlet 214 joined the conduit 27 at a point 3 cm up from the orifice 28 at the open end of conduit 27. The apparatus of FIG. 2 was run using the same materials as the experiment using the apparatus of FIG. 1, and at the same temperature and pressure, whilst compressed nitrogen at ca. 100 bar was introduced through side inlet 214 via valve 215, pressure being monitored using monitor 216. The junction 217 of the inlet 214 and conduit 27, and a short length of the inlet 214 upstream of the junction 217 is within the oven 22, to enable the nitrogen being introduced through inlet 214 to be preheated before meeting the contents of the conduit 27.

The vessel 19, 29 of the apparatus of both FIG. 1 and FIG. 2 may be opened to enable the collected particulate solute 111, 211 to be collected.

Using the apparatus of FIG. 2, i.e. with introduction of the pressurised gas, the product carbapenem 111, 211 deposited in the vessel 19, 29 was found to be in a desirable morphology comprising extremely small needle shaped crystals varying in length from 1 to 3 microns, i.e. smaller than those obtained via example 1 above and with good reconstitution properties. This advantageous formation of very small crystals may be attributable to the pressurised gas causing a back pressure in the conduit 27 such that particle formation occurred in a supercritical fluid region. The impurity profile of the drug substance product did not differ significantly from that of the input starting material and solvent residues were minimal.

EXAMPLE 3

Figure 3:
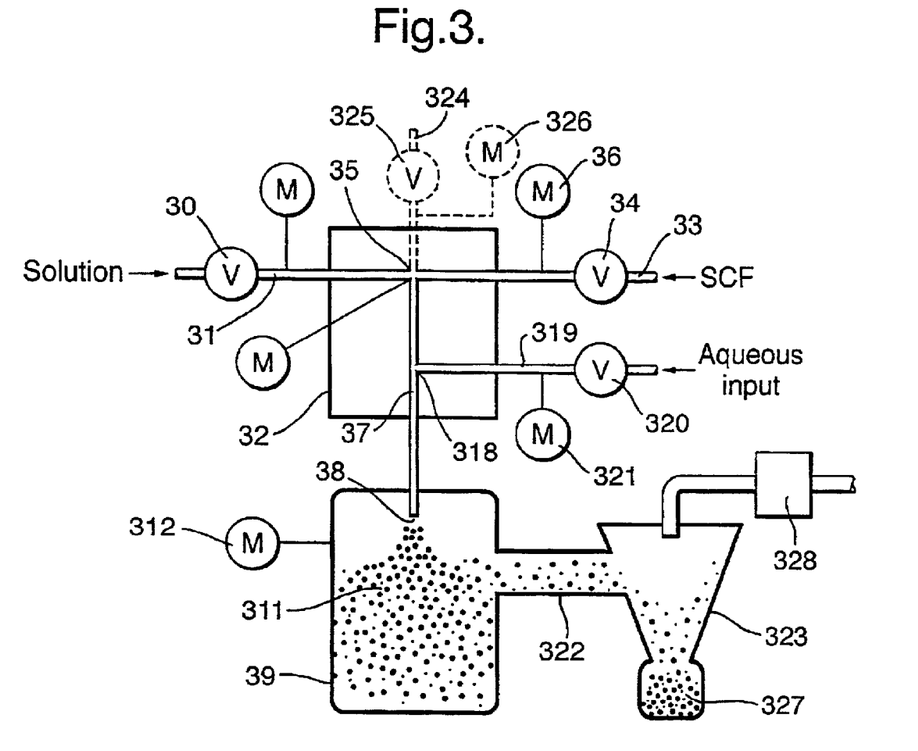

A further apparatus of the invention is shown in FIG. 3. In FIG. 3 parts corresponding to those of FIG. 1 are numbered correspondingly, (i.e. the features in FIG. 3 corresponding to features 10, 11, 12 etc. in FIG. 1 are numbered 30, 31, 32 etc. in FIG. 3).

In the apparatus of FIG. 3, a solution of the drug compound nabumetone and supercritical carbon dioxide are introduced into a "T" tube arrangement as in FIGS. 1 and 2, the internal bores of the inlet tubes 31, 33 being 0.75 mm. The mixed stream flows along conduit 37, which has an internal bore of ca. 0.5 mm (1/48 inch). At a point 318 located 2.4 cm from the junction 35 a side inlet 319 joins the conduit to form a "T" junction. Through the side inlet 319 a flow of a suspension comprising excipients made up with water was introduced. The flow of this mixture is controlled by valve 320 and monitor 321.

Downstream of the point 318 the length of the conduit 37 is kept to the minimum practical, and the internal bore is narrowed to 0.25 mm. The orifice 38 opens into the expansion chamber 39 in which pressure is monitored by monitor 312. The expansion chamber 39 does not incorporate a filter, but instead an outlet 322 leads to a cyclone 323 by means of which the particulate product 327 is collected, and a HEPA filter 328 by which the gaseous output exits to the atmosphere.

Using the apparatus of FIG. 3 the following experiment was performed. A solution phase of 16.0 g of the compound nabumetone dissolved in a mixture of 80 ml methanol and 120 ml acetone (a near saturated solution) was introduced at a rate of 3 ml/min into the limb 31 of the "T" tube. Carbon dioxide was introduced into the limb 33 of the "T" tube at a rate of 10 ml/min. The mixture was allowed to flow along the conduit 37 being the third limb of the "T" tube. The temperature control oven 32 was set to 100° C., but the precise temperature in the conduit 37 was not measured but was ca. 55° C., and the maximum measured pressure was 40 bar.

A suspension comprising 4.0 g of excipients such as matrix forming materials and surfactants dissolved in and made up to 200 ml with water was introduced at a rate of 3 ml/min into conduit 37 via inlet 319.

The mixture was allowed to spray out of the orifice 38 at the end of the conduit 37 into the collection chamber 39, the temperature of which was set to ca. 40° C., with an 100 internal pressure of atmospheric. The particulate product collected in the filter 323 was in the form of fine, spherical or semi-spherical white particles, being sub-20 micron size aggregates of a co-formulation of nabtunetone and the excipients, substantially anhydrous and with good dissolution characteristics. The proportion of nabumetone was consistent between 78.9–80.5% w/w over a number of runs of the process.

FIG. 3 also shows in hatched outline an alternative position for the side inlet at 324, instead of at the point 318. The arrangement at the junction 35 is an "X" tube system, with the aqueous substance being introduced into the point where the solution and supercritical fluid substance meet. Valve 325 and monitor 326 control the input of the aqueous substance at point 324. In this alternative construction the length of the conduit 37 between the junction 35 and the orifice 318 is kept minimal and the internal bore of the conduit is 0.25 mm.

Figure 4:
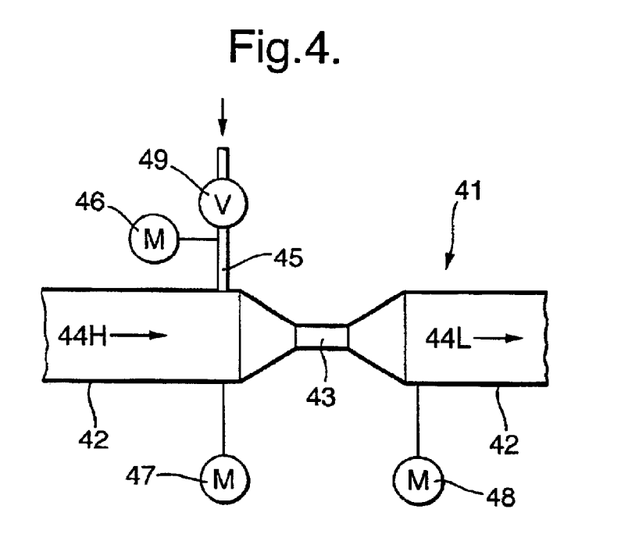

Referring to FIG. 4 a construction 41 suitable for the junction 217 of FIG. 2 is shown overall. The construction 41 comprises a conduit 42, being a pipe, e.g. the conduit 27 of FIG. 2, along which a flowing fluid (e.g. carbon dioxide at 200 bar and 80° C.) flows in the flow direction shown by the arrow 'A' from an upstream high pressure towards a downstream low pressure direction. There is a restriction 43 in the conduit, being a narrowing (e.g. of 150 micrometers diameter) in the cross sectional area of the pipe 42. In the region 44H upstream of the restriction 43 the flowing fluid is at a high pressure P1, and in the region 44L downstream of the restriction 43 the flowing fluid is at a pressure P2 lower than P1 (e.g, P1 being 200 bar and P2 being atmospheric). The cross sectional area of the restriction 43 at its narrowest is equal to or than that required to permit the maximum envisaged flowing fluid along the conduit 42, for example with the dimensions of the apparatus of FIGS. 1, 2 and 3, the envisaged maximum flow rate is 3 kg $CO_2$ per hour.

There is a means 45 being a side inlet pipe (e.g. 0.5 mm diameter), by which a flow control fluid (e.g. carbon dioxide at 200 bar and a temperature up to 200° C.) may be introduced into the conduit 42, at a pressure greater than or equal to the pressure P1 in the upstream region 44H. The inlet pipe 45 is located immediately upstream of the restriction 43.

The pressure, flow rate and temperature of the flowing fluid and the flow control fluid and other optional conditions such as the presence of solid or liquid particles or droplets (e.g. ice, dry ice or liquid carbon dioxide) downstream of the restriction 43, may be detected by monitors 46, 47, 48. The output signal from the monitors 46, 47 and 48 is passed to a control system (not shown) and used to control the device. For example the input of flow control fluid may be controlled by means of control valve 49 in inlet pipe 45. For example, the temperature of the flow control fluid may be controlled by means of an electrical heater or heat exchanger.

In use, a flow of flowing fluid is directed along conduit 42, and passes through restriction 43. Flow control fluid is introduced via inlet 45. If the pressure P3 of the flow control fluid is greater than the pressure P1 in the upstream region 44H, then the flow control generates a back pressure against the flow of the flowing fluid in the flow direction. This back pressure reduces the flow of the flowing fluid, and if the pressure P3 and the flow rate of the flow control fluid is high enough the flow of the flowing fluid through the restriction 43 may be controlled, minimised or for practical purposes, completely cut off so that in effect only the flow control fluid flows through the restriction 43.

The flow control fluid may be pre-heated before introduction into the upstream region 44 of the conduit 42, for example by means of the inlet pipe 45 passing through a pre-heater region (not shown) prior to its junction with conduit 42.

Although in FIG. 4 the downstream region 45 of the conduit 42 is shown as a pipelike continuation of the upstream region 44, region 45 could equally well be a vessel or other region at a lower pressure P2 than P1.

For example in a specific form of the device 41, the upstream region of the conduit 44H may be a pipe, the downstream region 44L may be an expansion vessel, such as 19, 29 and 39 of FIGS. 1, 2 and 3 at substantially ambient pressure and temperature, and the flow control fluid may be compressed carbon dioxide. The pressure P1 and temperature T1 in the upstream region 44H may be such that the carbon dioxide is in a supercritical state (T1>31° C. and P1>70 bar). Therefore such a device 41 may be located upstream, e.g. immediately upstream, of the orifice 18, 28, 38.

What is claimed is:

1. A process for the production of particles of a material wherein:

a stream of a dispersion of the material in a solvent and a stream of a compressible fluid antisolvent substance are brought into contact with each other so that the streams combine to form a mixture under conditions such that the substance is in compressible fluid antisolvent state, the mixture is then caused to flow along a conduit extending downstream from the region where the streams come into contact, toward an orifice which opens from the conduit directly into a downstream region so that the mixture flows through the orifice into the downstream region, a back pressure is generated in at least part of the conduit, whereby the pressure and temperature of the mixture in the conduit are such that the compressible fluid antisolvent substance remains in a compressed state over at least part of the length of the conduit, the conduit is sufficiently long that the residence time of the mixture in the conduit is such that particle formation occurs in the conduit, and the pressure and temperature in the downstream region are such that the compressible fluid antisolvent substance is present therein in a gaseous state and the material separates from the mixture in a particulate state as a consequence of the conversion of the compressible fluid antisolvent into a gas.

2. A process according to claim 1, wherein the compressible fluid antisolvent substance is in a supercritical fluid state over at least a part of the length of the conduit.

3. A process according to claim 1, wherein in the downstream region the pressure is in the range from 1–20 bar, and the temperature is in the range from 0–50° C.

4. A process according to claim 3, wherein, in the downstream region, the pressure is around atmospheric.

5. A process according to claims 1, wherein the compressible fluid antisolvent substance comprises carbon dioxide.

6. A process according to claim 5, wherein the carbon dioxide is in a supercritical fluid state over at least a part of the length of the conduit.

7. A process according to claim 1, wherein the solvent is an organic solvent selected from $C_{1-5}$ alkyl $C_{1-5}$ alkanoate esters, $C_{1-5}$ alcohols, and di- $C_{1-5}$ alkyl ketones, halogenated organic solvents, water, and mixtures thereof.

8. A process according to claim 1, wherein the solvent is saturated or near saturated with the material.

9. A process according to claim 2, wherein the ratio of the flow rate of the stream of said antisolvent substance in a supercritical fluid state to the flow rate of the stream of a dispersion of said material in a solvent is 50:1 or less.

10. A process according to claim 1, wherein one or more solid additives, are introduced, as a dispersion in a carrier vehicle, into the mixture of the material, the solvent and the compressible fluid antisolvent substance.

11. A process according to claim 1, wherein one or more additives, and/or modifiers, are included in the mixture of the material, the solvent and the compressible fluid antisolvent substance.

12. A process according to claim e 11, wherein the additive and/or modifier is introduced into the stream of dispersion of the material and/or the stream of a compressible fluid antisolvent susbstance.

13. A process according to claim 11, wherein the additive and/or modifier is mixed with one or both of said streams before the streams are brought into contact with each other.

14. A process according to claim 11, wherein the one or more additives and/or modifiers are separately introduced into the region where the streams are brought into contact with each other.

15. A process according to claim 11, wherein the one or more additives and/or modifiers are introduced into the mixture of the dispersion and the compressible fluid antisolvent substance at the region where the streams of the dispersion and compressible fluid antisolvent substance are brought into contact with each other.

16. A process according to claim 11, wherein the one or more additives and/or modifiers are introduced into the mixture of the dispersion and the compressible fluid antisolvent substance, in the conduit between the region where the streams come into contact and the orifice.

17. A process according to claims 11, wherein the one or more additives is an excipient material.

18. A process for the production of particles of a material wherein:

a stream of a dispersion of the material in a solvent and a stream of a compressible fluid antisolvent substance are brought into contact with each other so that the streams combine to form a mixture under conditions such that the substance is in compressible fluid antisolvent state, the mixture is then caused to flow along a conduit extending downstream from the region where the streams come into contact toward an orifice which opens from the conduit directly into a downstream region so that the mixture flows through the orifice into the downstream region, the pressure and temperature of the mixture in the conduit are such that the compressible fluid antisolvent substance remains in a compressed state over at least part of the length of the conduit, the pressure and temperature in the downstream region are such that the compressible fluid antisolvent substance is present therein in a gaseous state and the material separates from the mixture in a particulate state as a consequence of the conversion of the compressible fluid antisolvent into a gas, and one or more solid additives are introduced, as a dispersion in a carrier vehicle, into the mixture of the material, the solvent and the compressible fluid antisolvent substance, said compressible fluid antisolvent substance decompresses from said compressed state, and the one or more additives are introduced into the mixture of the dispersion and the compressible fluid antisolvent substance after said compressible fluid antisolvent substance decompresses.

19. A process for forming a co-formulation of a material and an additive in which a mixture of a material and an additive is produced by introducing the additive, in a fluid carrier vehicle, into a mixed stream in a compressed state, the mixed stream comprising the material and a compressible fluid antisolvent substance, and then causing the mixed stream, including the additive, to flow into a downstream region where the compressible fluid antisolvent substance decompresses, and wherein said material and said compressible fluid antisolvent substance are brought together at a location in a conduit, said mixed stream flows toward said downstream region in the conduit, a back pressure is maintained at least in a region of the conduit between said location and said downstream region, and the pressure and temperature of the mixed stream in the conduit are maintained, by said back pressure, at levels such that the compressible fluid antisolvent substance is maintained in a compressible fluid antisolvent state.

20. A process for forming a co-formulation of a material and an additive in which a mixture of a material and an additive is produced by introducing the additive, in a fluid carrier vehicle, into a mixed stream in a compressed state, the mixed stream comprising the material and a compressible fluid antisolvent substance, and then causing the mixed stream, including the additive, to flow into a downstream region where the compressible fluid antisolvent substance decompresses, and wherein said material and said compressible fluid antisolvent substance are brought together at a location in a conduit having an orifice, said mixed stream flows in the conduit toward said downstream region, and a pressurized gas is introduced into mixed stream in said conduit between said location at which the material and said compressible fluid antisolvent substance are brought together and the orifice.

21. A process for forming a co-formulation of a material and an additive in which a mixture of a material and an additive is produced by introducing the additive, in a fluid carrier vehicle, into a mixed stream in a compressed state, the mixed stream comprising the material and a compressible fluid antisolvent substance, and then causing the mixed stream, including the additive, to flow into a downstream region where the compressible fluid antisolvent substance decompresses, wherein said mixture flows through a conduit, the flow of the mixture in the conduit is restricted, by a restriction in the conduit between an upstream high pressure zone and a downstream lower pressure zone, and a flow control fluid is introduced into the conduit upstream of the restriction, the pressure of the flow control fluid being equal to or greater than the pressure of the mixture in the conduit upstream of the restriction.

22. A process for forming a co-formulation of a material and an additive in which a mixture of a material and an additive is produced by introducing the additive, in a fluid carrier vehicle, into a mixed stream in a compressed state, the mixed stream comprising the material and a compressible fluid antisolvent substance, and then causing the mixed stream, including the additive, to flow into a downstream region where the compressible fluid antisolvent substance decompresses, and wherein said mixture flows along a conduit, and a heat carrier fluid is introduced into the mixture flowing along the conduit.

23. A process for forming a co-formulation of a material and an additive in which a mixture of a material and an additive is produced by introducing the additive, in a fluid carrier vehicle, into a mixed stream in a compressed state, the mixed stream comprising the material and a compressible fluid antisolvent substance, and then causing the mixed stream, including the additive, to flow into a downstream region where the compressible fluid antisolvent substance decompresses, wherein the material in the mixed stream is dried in said downstream region, and wherein drying of said material is carried out by entraining particles of said material, in the downstream region, in a stream of gas.

24. An apparatus for the production of particles of a material, comprising:
    means (11, 13, 21, 23, 31, 33) for bringing a stream of a dispersion of the material in a solvent and a stream of a compressible fluid antisolvent substance into contact with each other such that the streams combine to form a mixture under conditions such that the antisolvent substance is in a compressible fluid antisolvent state,
    a conduit (17, 27, 37) along which the mixture can flow, the conduit extending downstream from the region where the streams are brought into contact with each other toward an orifice (18, 28, 38),
    means to cause the pressure and temperature of the mixture in the conduit (17, 27, 37) to be such that the substance remains in a compressible fluid antisolvent state along at least part of the conduit (17, 27, 37),
    a downstream region (19, 29, 39) in direct downstream communication with the orifice, and
    means to cause the pressure and temperature conditions in said downstream region to be such that the compressible fluid antisolvent substance in the downstream region is in a gaseous state,
    wherein the means (11, 13, 21, 23, 31, 33) for bringing a stream of a dispersion of the material in a solvent and a stream of a compressible fluid antisolvent substance into contact with each other, and the conduit (17, 27, 37), comprise a "T" or "Y" tube system (15, 25) having limbs for carrying said streams and a stem providing the conduit (17, 27).

25. An apparatus according to claim 24, wherein the limbs are joined at a junction, and wherein an orifice (18, 28, 38) is provided at an end of the stem remote from the junction (15, 25) of the limbs.

26. An apparatus for the production of particles of a material, comprising:
    means (11, 13, 21, 23, 31, 33) for bringing a stream of a dispersion of the material in a solvent and a stream of a compressible fluid antisolvent substance into contact with each other such that the streams combine to form a mixture under conditions such that the antisolvent substance is in a compressible fluid antisolvent state,
    a conduit (17, 27, 37) along which the mixture can flow, the conduit extending downstream from the region where the streams are brought into contact with each other toward an orifice (18, 28, 38),
    means to cause the pressure and temperature of the mixture in the conduit (17, 27, 37) to be such that the substance remains in a compressible fluid antisolvent state along at least part of the conduit (17, 27, 37),
    a downstream region (19, 29, 39) in direct downstream communication with the orifice,
    means to cause the pressure and temperature conditions in said downstream region to be such that the compressible fluid antisolvent substance in the downstream region is in a gaseous state, and
    introduction means (319, 325) for the introduction of one or more additive and/or modifiers,
    wherein the introduction means comprises an "X" tube arrangement (31, 33, 325, 37), comprising two limbs (31, 33) for introducing the respective streams of dispersion of material and compressible fluid antisolvent substance, a third limb (325) for introducing the additive and/or modifier, and wherein the conduit comprises a fourth limb (37).

27. An apparatus according to claim 26, wherein the introduction means comprises a further "T" or "Y" tube arrangement (37, 319), located downstream of the point where the dispersion and compressible fluid antisolvent substance are brought into contact with each other.

28. An apparatus for the production of particles of a material comprising:
    means (11, 13, 21, 23, 31, 33) for bringing a stream of a dispersion of the material in a solvent and a stream of a compressible fluid antisolvent substance into contact with each other such that the streams combine to form a mixture under conditions such that the antisolvent substance is in a compressible fluid antisolvent state,
    a conduit (17, 27, 37) along which the mixture can flow, the conduit extending downstream from the region where the streams are brought into contact with each other toward an orifice (18, 28, 38),
    means to cause the pressure and temperature of the mixture in the conduit (17, 27, 37) to be such that the substance remains in a compressible fluid antisolvent state along at least part of the conduit (17, 27, 37),
    a downstream region (19, 29, 39) in direct downstream communication with the orifice, and
    means to cause the pressure and temperature conditions in said downstream region to be such that the compressible fluid antisolvent substance in the downstream region is in a gaseous state,
    wherein the means to cause the pressure and temperature of the mixture in the conduit (17, 27, 37) to be such that the substance remains in a compressible fluid antisolvent state comprise the conduit (17, 27, 37) having dimensions such as to generate a back pressure in part or all of the conduit between the region where the streams are brought into contact with each other and the orifice (18, 28, 38).

29. An apparatus for the production of particles of a material comprising:

means (11, 13, 21, 23, 31, 33) for bringing a stream of a dispersion of the material in a solvent and a stream of a compressible fluid antisolvent substance into contact with each other such that the streams combine to form a mixture under conditions such that the antisolvent substance is in a compressible fluid antisolvent state, a conduit (17, 27, 37) along which the mixture can flow, the conduit extending downstream from the region where the streams are brought into contact with each other toward an orifice (18, 28, 38), means to cause the pressure and temperature of the mixture in the conduit (17, 27, 37) to be such that the substance remains in a compressible fluid antisolvent state along at least part of the conduit (17, 27, 37), a downstream region (19, 29, 39) in direct downstream communication with the orifice, and means to cause the pressure and temperature conditions in said downstream region to be such that the compressible fluid antisolvent substance in the downstream region is in a gaseous state, said apparatus also comprising pressurized gas introduction means (214) to introduce a pressurized gas directly into the conduit (27).

30. An apparatus for the production of particles of a material comprising:

means (11, 13, 21, 23, 31, 33) for bringing a stream of a dispersion of the material in a solvent and a stream of a compressible fluid antisolvent substance into contact with each other such that the streams combine to form a mixture under conditions such that the antisolvent substance is in a compressible fluid antisolvent state, a conduit (17, 27, 37) along which the mixture can flow, the conduit extending downstream from the region where the streams are brought into contact with each other toward an orifice (18, 28, 38), means to cause the pressure and temperature of the mixture in the conduit (17, 27, 37) to be such that the substance remains in a compressible fluid antisolvent state along at least part of the conduit (17, 27, 37), a downstream region (19, 29, 39) in direct downstream communication with the orifice, means to cause the pressure and temperature conditions in said downstream region to be such that the compressible fluid antisolvent substance in the downstream region is in a gaseous state, and drying means to dry particles of said material which are formed as a result of the mixture of said streams, wherein the drying means introduces a stream of heated air around the orifice.

\* \* \* \* \*